US012582804B2

(12) United States Patent
Ullrich et al.

(10) Patent No.: US 12,582,804 B2
(45) Date of Patent: Mar. 24, 2026

(54) TORQUE TRANSFER UNIT

(71) Applicant: Creo Medical LTD, Chepstow (GB)

(72) Inventors: George Christian Ullrich, Bethesda (GB); Steven Thomas, Chepstow (GB); Christopher Paul Hancock, Chepstow (GB); David Edward Webb, Bethesda (GB)

(73) Assignee: Creo Medical LTD, Chepstow (GB)

( * ) Notice: Subject to any disclaimer, the term of this patent is extended or adjusted under 35 U.S.C. 154(b) by 0 days.

(21) Appl. No.: 19/099,627

(22) PCT Filed: Aug. 2, 2023

(86) PCT No.: PCT/EP2023/071359
§ 371 (c)(1),
(2) Date: Jan. 29, 2025

(87) PCT Pub. No.: WO2024/028366
PCT Pub. Date: Feb. 8, 2024

(65) Prior Publication Data
US 2025/0256066 A1 Aug. 14, 2025

(30) Foreign Application Priority Data

Aug. 4, 2022 (GB) ...................................... 2211410

(51) Int. Cl.
*A61M 25/01* (2006.01)
*A61B 18/00* (2006.01)
(Continued)

(52) U.S. Cl.
CPC ................... *A61M 25/0136* (2013.01); *A61B 2018/00178* (2013.01); *A61B 18/1492* (2013.01);
(Continued)

(58) Field of Classification Search
CPC ........ A61M 25/0136; A61M 2205/586; A61M 2209/04; A61B 2018/001778;
(Continued)

(56) References Cited

U.S. PATENT DOCUMENTS

| 8,162,938 B2 * | 4/2012 | Smith | .............. A61B 17/32056 |
| | | | 606/113 |
| 2008/0108911 A1 * | 5/2008 | Palmer | ............ A61M 25/09041 |
| | | | 600/585 |

(Continued)

FOREIGN PATENT DOCUMENTS

| GB | 2523246 A | 8/2015 |
| WO | 2013/036900 A1 | 3/2023 |

OTHER PUBLICATIONS

International Search Report and Written Opinion, issued by the International Searching Authority in corresponding International Patent Application No. PCT/EP2023/071359, dated Nov. 17, 2023.
(Continued)

*Primary Examiner* — Linda C Dvorak
*Assistant Examiner* — Abigail Bock
(74) *Attorney, Agent, or Firm* — ArentFox Schiff LLP

(57) ABSTRACT

Various embodiments provide a torque transfer unit for rotating a flexible shaft. The torque transfer unit comprises an elongate track defining a track passage, and a key attachable to the flexible shaft and movable along the track passage. The key and the elongate track are configured to engage each other to inhibit relative rotation of the key and the track passage. The torque transfer unit is actuatable to selectively adjust an axial position of the key relative to the track passage. Some other embodiments provide a kit of parts.

17 Claims, 9 Drawing Sheets

(51) Int. Cl.
    *A61B 18/14*         (2006.01)
    *A61B 18/18*         (2006.01)

(52) U.S. Cl.
    CPC ................. *A61B 2018/1807* (2013.01); *A61B 2018/1861* (2013.01); *A61B 2218/002* (2013.01); *A61M 2205/586* (2013.01); *A61M 2209/04* (2013.01)

(58) Field of Classification Search
    CPC .... A61B 2018/1807; A61B 2018/1861; A61B 2218/002
    See application file for complete search history.

(56)                       References Cited

U.S. PATENT DOCUMENTS

| | | |
|---|---|---|
| 2010/0331621 A1 | 12/2010 | St. George et al. |
| 2020/0398031 A1 | 12/2020 | Gill et al. |

OTHER PUBLICATIONS

International Preliminary Report on Patentability, issued by the International Preliminary Examining Authority in corresponding International Patent Application No. PCT/EP2023/071359, dated Feb. 13, 2024.
Search Report Under Section 17(5), issued by the United Kingdom Intellectual Property Office in corresponding United Kingdom Patent Application No. GB2211410.2, dated Jan. 12, 2023.

* cited by examiner

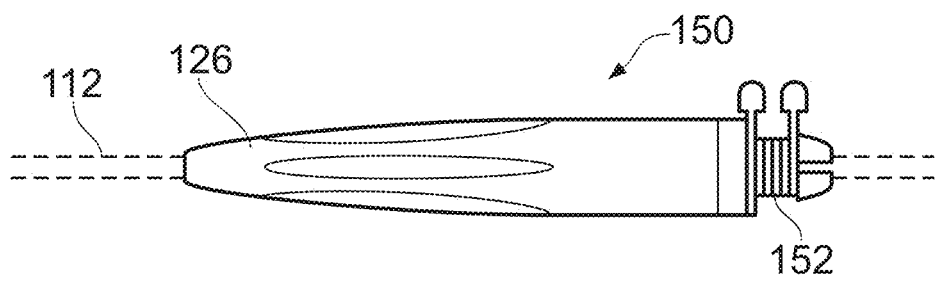
FIG. 8
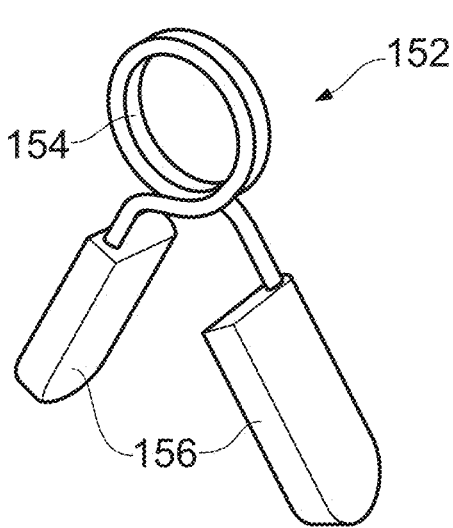
FIG. 9
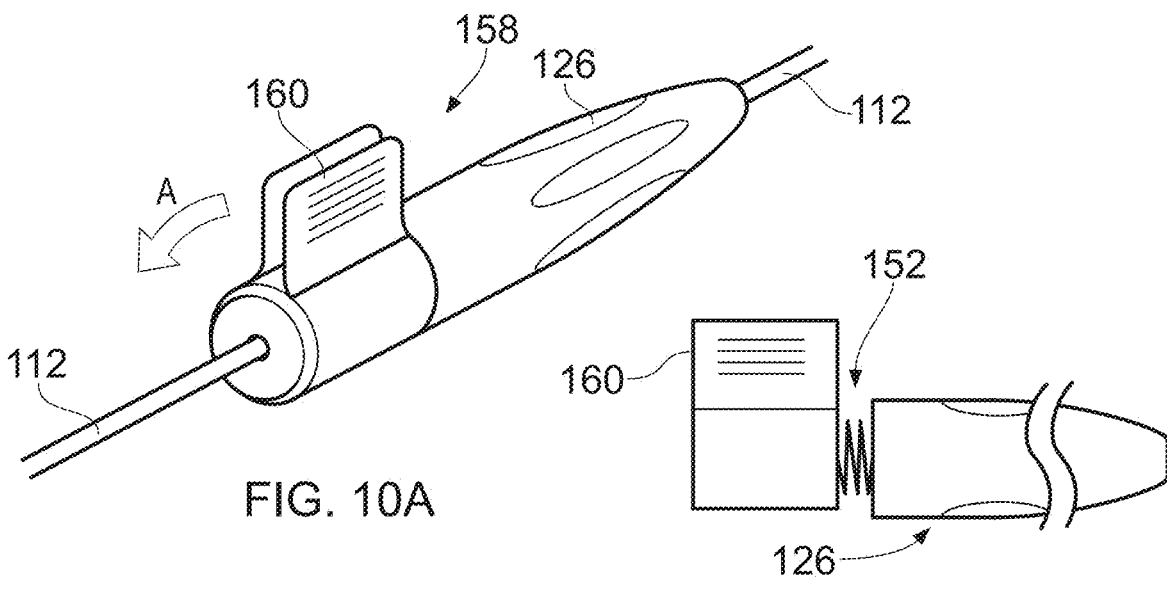
FIG. 10A
FIG. 10B

TORQUE TRANSFER UNIT

CROSS-REFERENCE TO RELATED APPLICATIONS

This application is a National Stage Entry of International Application No. PCT/EP2023/071359, filed Aug. 2, 2023, which claims priority to United Kingdom Patent Application No. 2211410.2, filed Aug. 4, 2022. The disclosures of the priority applications are hereby incorporated in their entirety by reference.

FIELD OF THE INVENTION

The present invention relates to a torque transfer unit for rotating an electrosurgical instrument, for example, during a surgical procedure. The electrosurgical instrument may be for delivering radiofrequency and/or microwave frequency energy into biological tissue.

BACKGROUND

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, bleeds are also undesirable, and need to be dealt with in an expedient manner, since the blood flow may obscure the operator's vision, which may prolong surgery and potentially lead to the procedure needing to be terminated and another method used instead, e.g. open surgery.

Electrosurgical generators are prevalent in hospital operating theatres, often for use in open and laparoscopic procedures, and increasingly for use with surgical scoping devices, e.g. an endoscope or the like. In endoscopic procedures the electrosurgical accessory is typically inserted through a lumen inside an endoscope. Considered against the equivalent access channel for laparoscopic surgery, such a lumen is comparatively narrow in bore and greater in length.

It is known to use microwave frequency energy for haemostasis (i.e. sealing broken blood vessels by promoting blood coagulation). Instruments are known that radiate microwave energy from the edges of a planar transmission line to cause localised tissue ablation or coagulation.

Additionally, instead of a sharp blade, it is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. In practice, an instrument is arranged to apply an RF voltage across the tissue matrix that is sufficient to generate heat within the cells to vaporise the water content of the tissue. However, as a result of this increasing desiccation, particularly adjacent to the RF emitting region of the instrument (which has the highest current density of the current path through tissue), direct physical contact between the tissue and instrument can be lost. The applied voltage then manifests itself as a voltage drop across this small void, which causes ionisation in the void that leads to a plasma. Plasma has a very high volume resistivity compared with tissue. The energy supplied to the instrument maintains the plasma, i.e. completes the electrical circuit between the instrument and the tissue. Volatile material entering the plasma can be vaporised and the perception is therefore of a tissue dissecting plasma.

GB 2 523 246 describes an interface joint for integrating into a single cable assembly all of (i) a fluid feed, (ii) a needle movement mechanism, and (iii) an energy feed (e.g. a cable supplying RF and/or microwave energy). The cable assembly may be sized to fit through the instrument channel of a conventional endoscope. Also described is a torque transfer unit for permitting controlled rotation of the cable assembly within the instrument channel of the endoscope.

The present invention has been devised in light of the above considerations.

SUMMARY OF THE INVENTION

The present invention provides a development to the concept discussed in GB 2 523 246.

At its most general, the inventors have developed a modified torque transfer unit for rotating a flexible shaft, e.g. for rotating an instrument tip (e.g. electrosurgical instrument tip) that is connected to the flexible shaft. The flexible shaft may be sized to fit through the instrument channel of a surgical scoping device, and may be connected to the instrument tip at its distal end.

According to the first aspect of the invention, there is provided a torque transfer unit for rotating a flexible shaft, the torque transfer unit comprising: an elongate track defining a track passage; and a key attachable to the flexible shaft and movable along the track passage, the key and the elongate track being configured to engage each other to inhibit relative rotation of the key and the track passage; wherein the torque transfer unit is actuatable to selectively adjust an axial position of the key relative to the track passage.

This arrangement effectively decouples the rotational control of the flexible shaft from the axial (longitudinal) adjustment of the torque transfer unit, thereby helping the torque transfer unit to securely hold the flexible shaft whilst also mitigating excess damage to the shaft. On one hand, since the track and key are configured to inhibit (e.g. prevent) relative rotation of the key within the track passage, they help ensure that the user's rotating force is efficiently transferred to the flexible shaft, without the shaft slipping relative to the torque transfer unit. On the other hand, since the torque transfer unit is actuatable to selectively adjust (move and secure) an axial position of the key relative to the track passage, it enables adjustment of the axial (longitudinal) position of the torque transfer unit on the flexible shaft to a position convenient for use. Since the, cooperation of the key within the elongate track helps prevent rotational slipping, the torque transfer unit may grip the shaft using less force, e.g. compared to arrangements which rely on a strong grip against the shaft in order to provide both rotational and axial control. This may in turn help to reduce strain and damage to the flexible shaft, since lower forces may be exerted on the shaft by the torque transfer unit.

As mentioned above, the torque transfer unit may be usable for rotating an electrosurgical instrument tip connected to the flexible shaft at a distal end of a surgical scoping device (e.g. endoscope) by transferring a user's rotating force to the flexible shaft, the torque transfer unit being arranged to impart a gripping force along a length of the flexible shaft that lies outside a proximal end of the surgical scoping device.

As used herein, the phrase "elongate track" may refer to a component that is configured to extend axially along a length of the flexible shaft. The elongate track may be tubular (e.g. extending entirely around the flexible shaft and key). Alternatively, the elongate track may extend around only a portion of the key, e.g. as a U-shaped track or otherwise. The track passage may have a smooth profile along its full length (e.g. as an elongate rectangular prism), for allowing the key to be adjusted across a continuous range of positions. Alternatively, the track passage may include one or more axial projections for securing an axial position of the key, as will be discussed further herein.

The elongate track may also be referred to as a "key runner". In arrangements where the elongate track is tubular, the key may be slidable within the track passage. In variant arrangements (e.g. for a track that does not extend fully around the flexible shaft and key), the key may be slidable alongside the track.

The key is movable relative to (along/within) the (first) passage of the elongate track. The key may be fixedly attached to the flexible shaft. However, it will be recognised that, in use, the track may be the element that is actually moved (relative to the key) to adjust the position of the torque transfer unit, while the key (and the flexible shaft) may remain stationary. Optionally, the key is fixed/adhered (e.g. glued, crimped) to the shaft, and thus will remain stationary relative to the shaft when in use.

The key may be formed of any suitable material (e.g. metal, plastic). For example, the key may be formed of a deformable material, e.g. metal, for crimping to the shaft.

As discussed above, the key and the elongate track are configured to engage each other to inhibit (e.g. prevent) relative rotation of the key and the track passage. In this regard, the "rotation" relates to a plane of rotation which is normal to the longitudinal axis of the flexible shaft. In other words, the key and the elongate track are configured to rotate together (by the same degree) about the longitudinal axis of the flexible shaft.

The key and the elongate track may be mutually configured to engage each other in any suitable manner to inhibit their relative rotation. The key may include one or more radial engagement structures that is configured to engage with a corresponding one or more radial engagement structures of the elongate track to inhibit relative rotation of the engagement structures.

As used herein, the phrase "engagement structure" may refer to a protrusion, edge, corner, pin, rib, groove, indentation, or other abutment surface that is configured to engage against a corresponding surface/structure of another component to prevent relative movement therewith. For example, the key may have one or more protrusions (e.g. corners) configured to engage against or interlock with a corresponding one or more protrusions (e.g. corners) of the elongate track.

A "radial" engagement structure may be configured to prevent relative radial movement, whereas an "axial" engagement structure may be configured to prevent relative axial movement. Accordingly, the phrase "radial engagement structure" may refer to an engagement structure (rib, groove, corner, etc.) formed at a particular location around a circumference/perimeter of a first component (e.g. the key), so as to provide the first component with a radius (e.g. as measured from the centre of the flexible shaft) that varies around its perimeter. The radial engagement structure may therefore act as a boundary/ledge which, when engaged against a corresponding structure of a second component (e.g. the elongate track), inhibits relative radial movement of the two components. A radial engagement structure may extend (e.g. continuously extend) along an axial direction of the component(s), to inhibit rotation along the full length of said component(s). A radial engagement structure may be e.g. a corner of a particular cross-sectional shape, as will be discussed further herein.

The torque transfer unit may be actuatable in any suitable manner to selectively adjust the axial position of the key relative to the track passage. For example, the torque transfer unit may comprise a clamping element connectable (e.g. connected) to the elongate track and actuatable to selectively adjust (move and secure) the axial position of the key relative to the track passage. The clamping element may be actuatable between: a clamped position for clamping onto the flexible shaft to thereby prevent axial movement of the elongate track relative to the key; and an unclamped position for unclamping the flexible shaft to thereby permit axial movement of the elongate track relative to the key Advantageously, providing a separate clamping element may allow adjustment of the key over a continuous range of positions. When the clamping element is in the unclamped position, the torque transfer unit may slide freely along a length of the flexible shaft to a position that is convenient for use. The unclamped position may also be referred to herein as a "release position". Once in the desired position, the torque transfer unit can be secured in place by actuating the clamping element to the clamped position.

In variant embodiments, the torque transfer unit may not require a distinct clamping element. For example, the elongate track itself may be actuatable to selectively adjust the position of the key, without requiring a clamping element to secure the position of the key relative to the track. For example, the elongate track may include one or more axial engagement structures configured to inhibit movement of the key and may be deformable to selectively permit movement of the key past the one or more engagement structures (as will be discussed further herein).

It may be advantageous to position the torque transfer unit as close as possible to the scoping device, in order to provide optimal control over the instrument tip at the distal end of the scoping device. In use, when the distal tip of the electrosurgical instrument is correctly positioned relative to the distal end of the flexible endoscope within the field of view on the endoscope's video monitor, it is intended that the endoscopist clamps and locks the torque transfer unit at the exit point of the flexible shaft from the endoscope working channel and immediately adjacent to the endoscope X-Y controls. When clamped in this location, the torque transfer unit may provide finger and thumb rotary and longitudinal positional control of the distal tip of the instrument.

Optionally, the clamping element has a gripping surface to facilitate grip by a user. The gripping surface may comprise one or more indentations, protrusions, and/or a concave profile sized to facilitate grip by the user. The gripping surface may be formed of a tacky and/or deformable material (e.g. silicone). The gripping surface may further improve ease of use, e.g. to facilitate actuation of the clamping element. The gripping surface may include one or more indentations/protrusions that extend in an axial direction.

This may be particularly useful to assist gripping in embodiments where the clamping element is rotatably actuatable about the axis of the shaft.

The clamping element may be configured to clamp onto the flexible shaft in any suitable manner. Optionally, the clamping element is rotatably actuatable between the clamped position and the unclamped position, e.g. by rotation of the clamping element about the flexible shaft. The clamping element may be sized to be rotatably actuatable by a thumb and forefinger of the user. Rotatable actuation may provide an intuitive and/or single-handed mechanism for actuating the clamping element, and may improve ease-of-use e.g. compared to arrangements requiring hinged actuation of a clamping element onto the flexible shaft.

Optionally, the clamping element defines a clamping passage for the flexible shaft to extend through, wherein the clamping element is actuatable to selectively tighten (grip) the clamping passage onto the flexible shaft. By providing a clamping passage that extends around the flexible shaft (e.g. around substantially an entire circumference thereof), the clamping element can improve the grip around the flexible shaft and distribute any forces evenly around the shaft.

Where present, the clamping passage may be axially spaced from and/or concentric with the track passage.

The clamping element may be a collet-type clamp. As used herein, the term 'collet' takes its usual meaning referring to a subtype of chuck that forms a collar around an object to be held and exerts a strong clamping force on the object when it is tightened.

The collet-type clamping element may include a collet element defining the clamping passage for the flexible shaft, and an actuating element (e.g. threaded or spring-loaded actuating element) that is actuatable to selectively tighten or loosen the collet element (and thus the clamping passage) around the flexible shaft. The collet element may be distinct from the actuating element, i.e. they may be formed as separate components. Alternatively, the clamping element may be a collet-type clamp having a unitary construction, e.g. as a torsional spring that defines the clamping passage therethrough and has axially protruding end portions which are actuatable (e.g. squeezable) to vary the size of the clamping passage.

Optionally, the clamping element is a threaded collet-type clamp. For example, the actuating element may have a threaded surface (e.g. an inner threaded surface), the collet element may have a cooperating threaded surface (e.g. an outer threaded surface). In use, the thread of the actuating element engages with the thread of the collet element such that rotation of the actuating element tightens the collet element against the flexible shaft. The collet and/or actuating element may have a tapered form to facilitate this tightening. Also, the actuating element may include the gripping surface on its outer surface to facilitate its rotation by a user (which may be configured similarly to the gripping surfaces already discussed above). This may help to firmly hold the flexible shaft, in a simple and easily adjustable manner.

Optionally, the clamping element comprises a resilient member (e.g. torsional spring) that is resiliently biased towards the clamped position. This can improve ease of use and helps to ensure that the torque transfer unit remains axially secured when in use.

For example, in embodiments where the clamping element is a spring-loaded collet type clamp, the clamping element may comprise a torsion spring defining the clamping passage. The clamping element may comprise a lever connected to an end of the torsional spring and actuatable to unwind the spring and thereby increase the size of the passage. Preferably, the clamping element comprises a single lever that is actuatable by rotating about the axis of the flexible shaft. This can easily be pushed by the user's thumb for simple adjustment. Alternatively, the clamping element may comprise two levers (one connected to each end of the torsion spring) and may be actuatable by squeezing the levers together (e.g. using two fingers). This may also be referred to as a "squeeze-and-release" mechanism.

In variant embodiments, the clamping element may not be a collet-type clamp. For example, the clamping element may alternatively comprise a hinged clamp. For example, the clamping element may comprise a first jaw and a second jaw, the first jaw being movable (e.g. pivotable) relative to the second jaw to clamp onto the flexible shaft; and a retaining member that is actuatable to retain the first jaw in the clamped position or to release the first jaw from the clamped position.

The first jaw and the second jaw may together form a substantially U-shaped member. The U-shaped member may include an aperture for conveying the flexible shaft therethrough (between the first and second jaws).

The retaining element may be configured to snap-fit against the first jaw to retain the first jaw in the clamped position. The retaining element may be configured to extend from an end of the second jaw, towards a free end of the first jaw (i.e. across the open end of the U-shaped member), and may comprise a hook for engaging against (snap-fitting against) the free end of the first jaw in the clamped position. Optionally, the retaining element is located at the proximal end of the torque transfer unit. This may facilitate simple and one-handed operation. In use, the retaining element may be simply pulled back (in a proximal direction) to release the hook from the first jaw, thereby allowing the first jaw to move away from the second jaw, in turn unclamping the flexible shaft.

In this embodiment, the clamped position may also be referred to as a "closed" position (referring to a position in which the jaws are close together), and the unclamped position may also be referred to as an "open" position (a position in which the jaws are further apart).

Optionally, the retaining element and the U-shaped member are integrally formed (e.g. as a single plastic element). Such a clamping element may be relatively inexpensive and easy to manufacture.

Optionally, the clamping element (e.g. the retaining element and/or first jaw) may be pliant, so that the retaining element and/or first jaw may be resiliently deformed towards/away from the second jaw to actuate between the clamped/unclamped positions. Optionally, the first jaw may be resiliently biased towards the unclamped (open) position. This may facilitate one-handed release of the clamping element from the clamped position, since the first jaw may resiliently return (snap-back) to an open position immediately upon release of the retaining element from the first jaw.

The first and/or second jaw may include one or more protrusions (e.g. teeth) that are configured to bear against the flexible shaft when the clamping element is in the clamped position. This may further improve the grip of the clamping element, forming a tight frictional fit against the flexible shaft in order to prevent its movement. The first and/or second jaws (including any teeth thereof) may together define a clamping passage as described above. Optionally, the protrusions (teeth) may have a curved inner surface for engaging around a circumference of the flexible shaft. This may help to improve the grip around the flexible shaft. Optionally, the first and/or second jaw may include teeth that are axially offset (staggered, interlocking) relative to each other, e.g. such that one of the jaws includes a tooth that is locatable axially between a pair of teeth of the other jaw. This may help to squeeze/compress the flexible shaft between the jaws.

Optionally, the torque transfer unit may further comprise an outer cover around the elongate track, the cover including a gripping surface to facilitate grip by a user. This may help to further improve the user's control of the instrument. The gripping surface may be configured similarly to that described above in relation to the clamping element, e.g. having one or more indentations, protrusions, and/or a concave profile sized to facilitate grip by the user. Alternatively or in combination, the gripping surface may comprise a deformable or tacky material (e.g. silicone) to facilitate grip.

Optionally, an outer surface of the elongate track and an inner surface of the cover may be configured to engage each other to inhibit (e.g. prevent) rotation and/or axial movement of the elongate track relative to the cover. This may further improve the control of the torque transfer unit, by inhibiting slipping of the track within the cover and thereby more effectively transferring a user's rotational and/or axial forces to the flexible shaft.

The elongate track and the cover may be configured to engage each other in any suitable manner. For example, an outer surface of the elongate track and/or an inner surface of the cover may include one or more engagement structures similar to those discussed above in relation to the key and the elongate track.

The cover may be formed of a relatively rigid or deformable material. Accordingly, the cover may have a pre-formed engagement structure (e.g. formed of a relatively rigid material such as plastic) configured to engage with/against the engagement structure of the elongate track, or the cover may be formed of a deformable material configured to deform against the elongate track to form a close fit against its engagement structure(s).

In some embodiments, the torque transfer unit may be actuatable without requiring a clamping element. For example, in some embodiments, the torque transfer unit may be actuatable by sliding the elongate track relative to the key, in turn overcoming a resistive frictional force between the axial engagement structure against the key. For example, optionally, the torque transfer unit may comprise an axial engagement structure (or a plurality thereof) along the track passage. The axial engagement structure(s) may be configured in a similar manner to the axial engagement structures already discussed above, for engaging against the key to inhibit relative axial movement of the key past the engagement structure. The elongate track (e.g. the axial engagement structure(s)) may be resiliently deformable (e.g. formed of silicone) to selectively permit movement of the axial engagement structure past the key by deforming the elongate track. In other words, the elongate track may be resiliently deformable between a non-deformed state in which the axial engagement structure inhibits relative movement of the elongate track past the key, and a deformed state in which the elongate track is slidable past the key (e.g. due to the axial engagement structure being resiliently deformed such that it can slide over the key).

The torque transfer unit may therefore be actuated simply by axially sliding the elongate track relative to the flexible shaft. When the elongate track is pulled/pushed with sufficient force, the force of the key against the axial engagement feature can deform the axial engagement feature, thereby allowing it to move past the key to adjust the axial position of the torque transfer unit. A torque transfer unit configured in this manner may be relatively simple and cheap to manufacture, since it does not require a further component in the form of a clamping element in order to adjust the position of the key.

Optionally, the elongate track may include a plurality of axial engagement structures along the track passage. For example, the track passage may have an undulating (e.g. scalloped or zig-zag) profile for engaging against the key (which may have a complementary profile). Such an arrangement with a plurality of engagement structures may allow the position to be adjusted along a plurality of discrete increments. In contrast, the clamping elements described above may allow for continuous position adjustment.

The elongate track may be formed as part of a unitary grippable member which is shaped on its inner surface to provide the track passage, and which is shaped on its outer surface to providing a gripping surface. This unitary member may include similar features to the above-referenced "outer cover", except in that the grippable member is integral with the elongate track.

Optionally, the torque transfer unit may further include the flexible shaft. The key may be attached (e.g. permanently attached, fixed) to the flexible shaft. The key may be attached to the flexible shaft in any suitable manner. For example, the key be a collar that fits around a circumference of the flexible shaft, e.g. by a tight interference fit. Alternatively, the key may be attached to the flexible shaft in other manners, e.g. by using an adhesive and/or welding. By attaching the key to the flexible shaft, the torque transfer unit may prevent the key from slipping about the flexible shaft, thereby improving rotational control.

It will be noted that, if the key is permanently attached the flexible shaft, the location of the key on the flexible shaft will constrain the extent to which the torque transfer unit may be axially adjusted along the flexible shaft. Therefore, in order to facilitate use with a variety of surgical scoping devices (which may each have different lengths requiring different positions of the torque transfer unit on the flexible shaft), it may be desirable to also provide a kit of parts, the kit of parts having a plurality of flexible shafts, and a plurality of torque transfer units, wherein each key of each torque transfer unit is permanently attached to a respective flexible shaft at a different position along the flexible shaft.

The flexible shaft may also be referred to herein as a "flexible sleeve". The flexible shaft may convey a coaxial cable and/or a fluid channel therethrough, for delivery of EM energy and/or fluid to biological tissue. The shaft may be connected at its distal end to an electrosurgical instrument tip. As used herein, the term "proximal" may refer to a region away from the instrument tip. Conversely, the term "distal" may refer to a region located closer to the instrument tip.

The electrosurgical instrument tip may be any device which in use is arranged to use RF EM energy and/or microwave frequency EM energy for the treatment of biological tissue. The electrosurgical instrument may use the RF EM energy and/or microwave frequency EM energy for any or all of resection, coagulation and ablation. For example, the instrument may be a resection device as disclosed in GB 2 523 246 A, but alternatively may be any of a pair of microwave forceps, a snare that radiates microwave energy and/or couples RF energy, and an argon beam coagulator.

Herein, radiofrequency (RF) may mean a stable fixed frequency in the range 10 kHz to 300 MHz and microwave frequency may mean a stable fixed frequency in the range 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz. Preferred spot frequencies for the microwave energy include 915 MHz, 2.45 GHz, 5.8 GHz, 14.5 GHz, 24 GHz.

Optionally, the flexible shaft may include a reinforced section that is stiffer or thicker than a more distal section of the flexible shaft (e.g. a section insertable through the surgical scoping device). The key may be attachable to the reinforced section of the flexible shaft. This arrangement may help to further reduce stress or damage to the shaft. Additionally, the reinforced section may help to provide better rotational control of the instrument, since a stiffer/ thicker section may be less prone to coiling up, thereby helping to ensure that rotation of the shaft is effectively transferred to the instrument tip rather than potentially causing the shaft to coil-up outside the scoping device. In embodiments where the reinforced section is thicker than a more distal section inside the scoping device, the added thickness may also act as a stopper to prevent over-exertion of the instrument tip through the scoping device. More information regarding suitable reinforced shafts may be found in co-pending GB application no. 2119001.2, which is incorporated herein by reference in its entirety.

Optionally, the key may be a collar defining a collar passage for the flexible shaft to extend through. The collar passage may be concentric with the track passage and, if present, the clamping passage. Configuring the key as a collar may help to provide a stronger attachment around the flexible shaft (e.g. entirely around a full 360° of the flexible shaft), thereby helping to provide more stable control of the flexible shaft compared to a key that is attachable to only one side of the flexible shaft. Configuring the key as a collar may also advantageously enable a larger outer surface of the key to engage against the elongate track, which may in turn help to inhibit/prevent rotational slipping of the key relative to the track.

In variant embodiments, which are not illustrated, the key may be configured differently, e.g. as a u-shape structure attachable along only one (half) side of the flexible shaft. In some other embodiments, the attachable proportion of the key is between a half circumference and a full circumference of the shaft, or is less than one half circumference of the shaft. For example, the key may include multiple discrete attachment portions distributed around all or part of the shaft's circumference.

As mentioned above, the track and key may have cooperating (e.g. complementary and/or interlocking) cross-sectional shapes that define one or more radial engagement structures (e.g. corners) which are configured to engage each other to inhibit relative rotation of the track and key. An outer surface of the key may have a polygonal cross-sectional shape that is complementary to a cross-sectional shape of an inner surface of the track passage of the elongate track. In this context, an "outer surface" may refer to a surface that faces radially away from the flexible shaft in use, and an "inner surface" may refer to a surface that faces radially toward the flexible shaft in use. The key may therefore have one or more corners on its outer surface configured to engage with a corresponding one or more corners of the track passage. This engagement may function to inhibit relative rotation of the key within the track passage.

For example, an outer surface of the key (e.g. collar) may have a rhombus ("diamond") or rectangular (e.g. square)

cross-sectional shape (as viewed along the axis of the shaft), and an inner surface of the elongate track may have a complementary rhombus or rectangular (e.g. square) cross-sectional shape for inhibiting relative rotation with the key. Such a cross-sectional shape may provide a convenient arrangement for preventing relative rotation, while also enabling relative axial movement of the collar within the track. Further, a square shape may help to improve compactness and rotationally symmetry. The key may form a close/tight fit against the track passage of the elongate track, to help inhibit relative rotation.

In variant embodiments, the key and elongate track may have other cross-sectional shapes which inhibit relative rotation between the key and elongate track (e.g. triangular, hexagonal, octagonal, irregular, oval, eccentric, etc.).

Optionally, the track passage terminates in an axial engagement structure for preventing axial movement of the key beyond the track passage. In particular, the track passage may terminate in a narrowed section for retaining the key along the track passage. The narrowed section may further facilitate adjustment of the torque transfer unit by preventing the elongate track from sliding off the key during axial adjustment. The narrowed section and the key may be cooperatively shaped to abut each other to prevent movement of the key past the narrowed section. The narrowed section may define an opening for conveying the flexible shaft, said opening being smaller than the key, to prevent movement of the key from the track passage.

Optionally, the track passage may terminate in said narrowed section(s) at its proximal and/or distal ends, to prevent separation of the elongate track from the key in a proximal and/or distal direction. The narrowed section(s) may be part of the elongate track itself, or may be part of a different element that abuts the elongate track (e.g. the clamping element).

In contrast to the deformable axial engagement structures discussed in relation to the deformable track embodiment (which are located along the track passage rather than at its ends), the narrowed section(s) at the end(s) of the track may be sufficiently rigid (non-deformable) to prevent their movement past the key.

Preferably, the length of the elongate track is longer than the length of the key. This allows the elongate track to be moved relative to (e.g. slid over) the key (e.g. while the key is attached to the flexible shaft) to adjust the position of the torque transfer unit on the flexible shaft. Optionally, the elongate track has a length that is at least three times longer than a length of the key, more preferably at least four times longer than the length of the key, more preferably at least five times longer than the length of the key. By increasing the ratio of the length of the elongate track compared to the length of the collar, the torque transfer unit may be adjusted over a greater range of positions on the flexible shaft.

Optionally, the elongate track comprises a first track portion and a second track portion, the first and second track portions being mutually connectable to form the elongate track. Providing a two-part track can help to facilitate insertion of the key (e.g. collar) inside the track. This may be particularly convenient, for example, in embodiments where the elongate track is a tubular track (having a first tubular track portion and a second tubular track portion) terminating in a narrowed section that otherwise would not be able to receive the key therethrough. The first and second track portions may be configured to connect in any suitable manner, e.g. by interference fit, snap-fit engagement, threaded engagement, or otherwise.

Optionally, the first track portion includes an enlarged section for receiving and connecting with the second track portion. The enlarged section may help to reinforce the junction between the first and second track portions, by receiving and stabilising a section (e.g. a distal or proximal section of) the second track portion. The enlarged section may also function as an engagement structure to prevent axial sliding of the elongate track relative to an outer cover, as will be discussed further below.

In embodiments having an outer cover, optionally, the elongate track may include an enlarged section (e.g. as part of a first track portion, as discussed above), defining one or more axial engagement structure(s) configured to engage the cover (e.g. a corresponding axial engagement structure thereof) to prevent axial movement of the elongate track relative to the cover. For example, the enlarged section may terminate in one or more ledges at its proximal and/or distal ends, which may function as axial engagement structures.

As used herein, the phrase "axial engagement structure" may refer to an engagement structure (e.g. rib, groove, edge, protrusion, indentation) formed at a particular axial position (in the proximal/distal direction) of a component (e.g. elongate track). A first axial section (e.g. proximal section) of the component may therefore protrude relative to a second axial section (e.g. distal section) of the component, which may help to inhibit axial movement of the component when engaged with a corresponding structure.

An axial engagement structure may extend in a radial (angular) direction around the component, whereas a radial engagement structure may extend in an axial direction along the component.

Optionally, the elongate track may include a radial engagement structure configured to engage the cover (e.g. a corresponding radial engagement structure thereof) to prevent radial slipping of the elongate track within the cover. Radial engagement structure(s) may be provided, for example, by any corners/bends/abutments along an outer cross-sectional shape of a component.

For example, optionally, at least a portion of the elongate track may include a cross-sectional outer shape (e.g. rhombus, rectangular, or square cross-sectional shape) that is configured to engage with an inner surface of the cover to prevent relative rotation. The cross-sectional shape may be defined from a direction along the axis of the flexible shaft. The cross-sectional shape may include one or more corners/bends that function as a radial engagement structure as discussed above.

The radial engagement structure(s) may extend continuously along the entire length of the elongate track (thereby preventing rotational movement without in turn also preventing axial movement). However, preferably, the radial engagement structure(s) does not extend along the entirety of the elongate track, and thus terminates in the axial direction, thereby also forming an axial engagement structure that may inhibit axial movement of the component. For example, the enlarged section of the elongate track (discussed above) may comprise the radial protrusion, e.g. as part of its cross-sectional shape, such that the enlarged section may include both axial and radial engagement structures.

Optionally, the present disclosure also provides a system or a kit of parts including the torque transfer unit described above in combination with an interface joint for interconnecting an electrosurgical generator, a fluid supply, and an electrosurgical instrument tip, the interface joint comprising: a housing having: an electrical inlet for receiving radiofrequency (RF) electromagnetic (EM) energy and/or microwave frequency EM energy from the electrosurgical generator; a fluid inlet for receiving fluid from the fluid supply; and an outlet; and the flexible shaft, wherein the flexible shaft is configured to connect the outlet to the instrument tip, the flexible shaft having: a coaxial cable that is connected to the electrical inlet; and a fluid channel that is in fluid communication with the fluid inlet. For example, the interface joint may be an interface joint as described in GB 2 523 246.

The invention includes the combination of the aspects and preferred features described except where such a combination is clearly impermissible or expressly avoided.

SUMMARY OF THE FIGURES

Example embodiments illustrating the principles of the invention will now be discussed with reference to the accompanying figures in which like numerals denote like elements.

FIG. 8 is a side view of a variant torque transfer unit having a torsional spring collet type clamping element;

FIG. 9 is a perspective view of a torsional spring suitable for the use in the torque transfer unit of FIG. 8;

FIGS. 10A and 10B are side and perspective views, respectively, of an alternative torque transfer unit having a torsional spring collet type clamping element with a single lever;

DETAILED DESCRIPTION OF THE INVENTION

Aspects and embodiments of the present invention will now be discussed with reference to the accompanying figures. Further aspects and embodiments will be apparent to those skilled in the art. All documents mentioned in this text are incorporated herein by reference.

Figure 1:
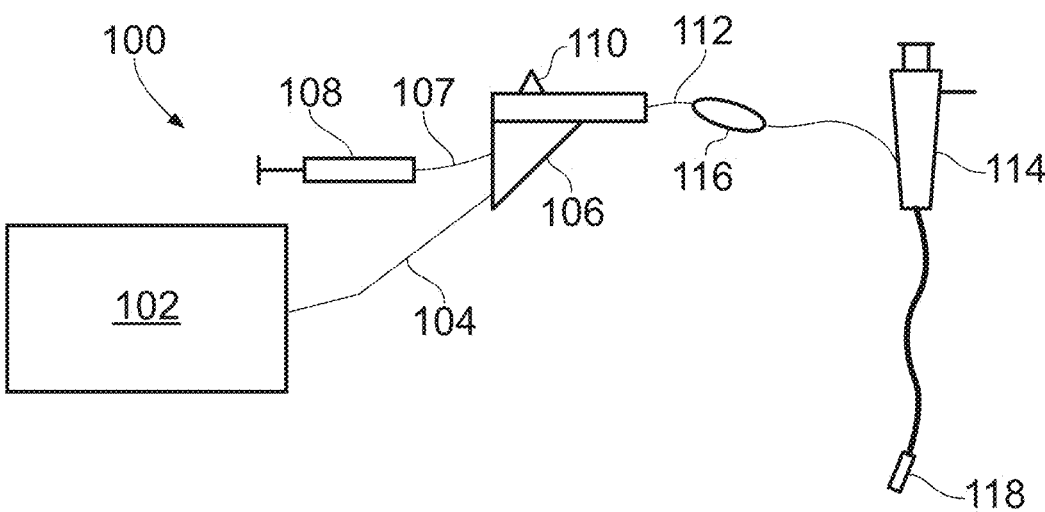
FIG. 1 is a schematic view of a complete electrosurgery system in which the present invention may be applied.

FIG. 1 is a schematic diagram of a complete electrosurgery system 100 that is capable of selectively supplying to the distal end of an invasive electrosurgical instrument any or all of RF energy, microwave energy and fluid, e.g. saline or hyaluronic acid. The system 100 comprises a generator 102 for controllable supplying electromagnetic (EM) energy. In the present embodiment, the EM energy includes RF EM energy and/or microwave frequency EM energy. A suitable generator for this purpose is described in WO 2012/076844, which is incorporated herein by reference.

The generator 102 is connected to an interface joint 106 by an interface cable 104. The interface joint 106 is also connected to receive a pressurised fluid supply from a fluid delivery apparatus 108 via a fluid supply cable 107. The function of the interface joint 106 is to combine the inputs from the generator 102 and fluid delivery device 108 into a single flexible shaft 112, which extends from the distal end of the interface joint 106. It is to be understood that the shaft 112 may form part of the interface joint 106.

The flexible shaft 112 is insertable through the entire length of an instrument (working) channel of a surgical scoping device 114. A torque transfer unit 116 may be mounted on a proximal length of the shaft 112 between the interface joint 106 and surgical scoping device 114. The torque transfer unit 116 engages the shaft to permit it to be rotated within the instrument channel of the surgical scoping device 114. The configuration of the torque transfer unit 116 is discussed in more detail below.

The flexible shaft 112 has an electrosurgical instrument tip 118 that is shaped to pass through the instrument channel of the surgical scoping device 114 (e.g. an endoscope) and protrude (e.g. inside the patient) at the distal end of the instrument channel. The instrument tip includes an active tip for delivering RF EM energy and/or microwave EM energy into biological tissue and an aperture for delivering pressurised fluid (e.g. saline, Gelofusine, and/or hyaluronic acid with added marker dye). These combined technologies provide a unique solution for cutting and destroying unwanted tissue and the ability to seal blood vessels around the targeted area. By applying pressure to the fluid, the surgeon is able to inject the fluid between tissues layers in order to distend and mark the position of a lesion to be treated. The injection of fluid in this manner lifts and separates the tissue layers making it both easier to resect around the lesion and plane through the submucosal layer, reducing the risk of bowel wall perforation and unnecessary thermal damage to the muscle layer.

The instrument tip 118 further includes a protective hull positioned under the active tip to assist a tissue planing type resection action, again helping to protect against inadvertent perforation and ensure viability of the remaining tissue, which in turn facilitates more rapid healing and post operation recovery.

The structure of the instrument tip 118 may be particularly designed for use with a conventional steerable flexible endoscope having a working channel with an internal diameters of at least 2.2 mm and a working length of between 60 cm and 170 cm. As such the majority of the comparatively small diameter instrument is housed within the lumen of a much larger and predominantly polymer insulating device, i.e. the flexible endoscope channel. In practice, only 5 mm to 25 mm of the distal assembly protrudes from the distal end of the endoscope channel, in order not to block the field of view or adversely affect camera focussing. The protruding part of the distal assembly is the only portion of the instrument that ever makes direct contact with the patient.

At the proximal end of the endoscope working channel, which is typically held 50 cm to 80 cm from the patient, the flexible shaft 112 emerges from the working channel port and extends a further 30 cm to 100 cm to the interface joint 106. In use, the interface joint 106 is typically held by a gloved assistant throughout the procedure. The interface cable 104 is connected to the generator 102 using a QMA-type coaxial interface, which is designed to allow continuous clockwise or counter clockwise rotation. This permits the interface joint 106 to rotate with the torque transfer unit 116 under the control of the user. The assistant supports the interface joint 106 throughout the procedure in order to assist the user with sympathetic instrument rotation and fluid injection.

Figure 2:
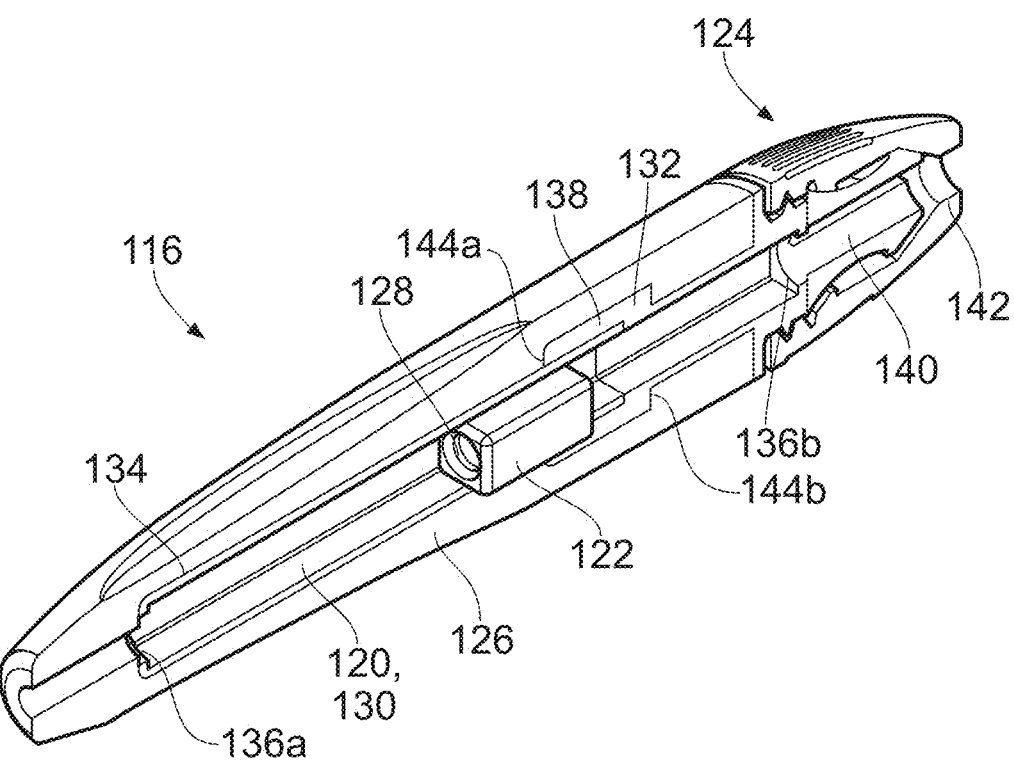
FIG. 2 is a perspective cutaway view of a torque transfer unit that is an embodiment of the invention, (with the key being shown in full rather than in cutaway)
Figure 4:
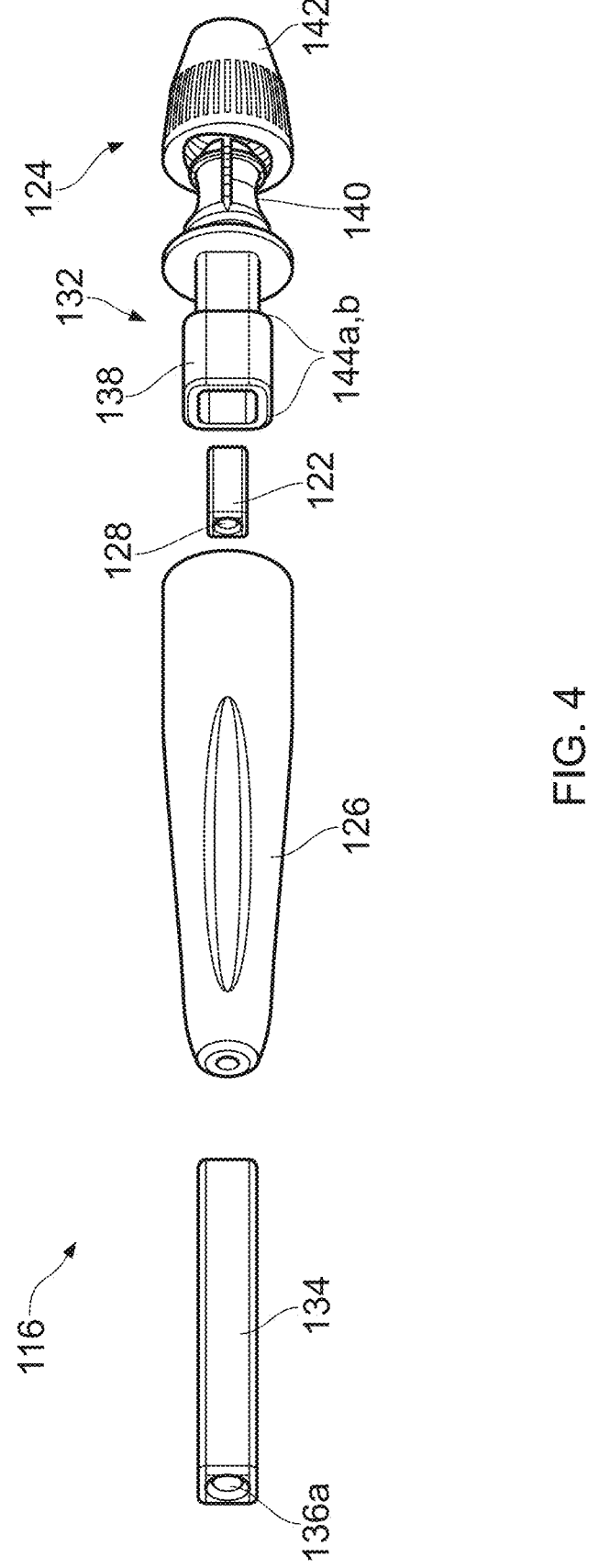
FIG. 4 is an exploded side view of the torque transfer unit shown in FIG. 2.
Figure 5:
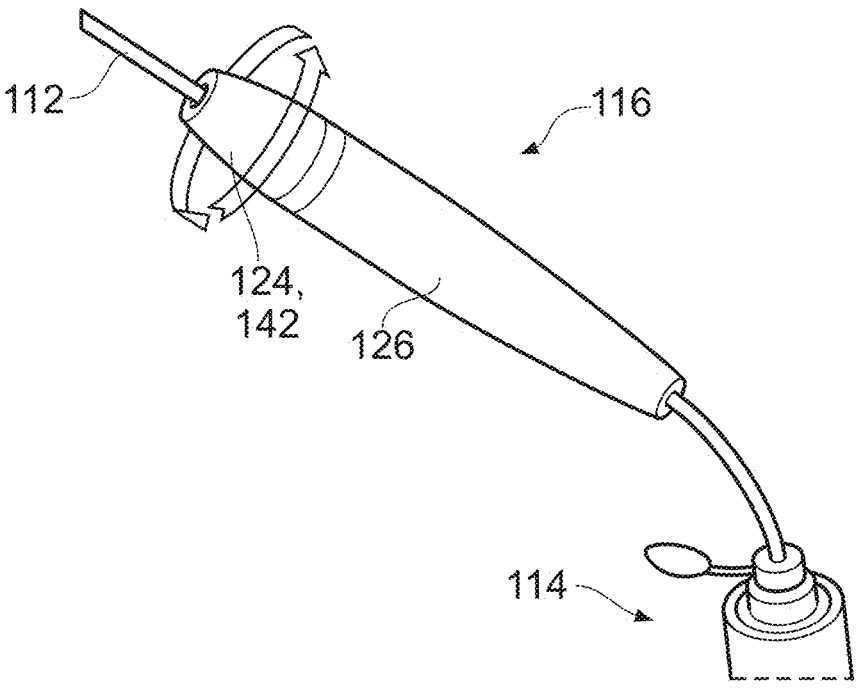
FIG. 5 is a perspective view of the torque transfer unit shown in FIG. 2 connected to a flexible shaft outside a surgical scoping device.

FIG. 2 is a perspective cutaway view showing the torque transfer unit 116 according to one embodiment of the invention. FIGS. 3 to 5 show further details of the torque transfer unit 116.

The torque transfer unit 116 has an elongate track 120, a key 122, a clamping element 124, and a cover 126. (For illustrative purposes, it is noted that FIG. 2 shows all elements of the torque transfer unit 116 in cutaway view, except for the key 122 which is shown in full.)

In this embodiment, the key 122 is configured as a collar arranged to fit around a circumference of the flexible shaft (e.g. the shaft 112 of FIG. 1). The key 122 therefore defines a key passage 128 (also referred to as a collar passage) for receiving the flexible shaft therethrough. The key passage 128 has a circular cross-section configured to form a close fit (e.g. an interference fit) around the flexible shaft.

On its outer surface, the key 122 has a polygonal (e.g. square, rhombus, rectangular) cross-sectional shape (as viewed along the longitudinal axis of the flexible shaft) which forms radial engagement structures in the form of a plurality (e.g. four) outer corners. In this embodiment, the key 122 fits entirely within the elongate track 120, which is a tubular track defining a track passage 130 that is axially movable relative to the key 122. On its inner surface, the elongate track 120 (i.e. the track passage 130) has a polygonal (e.g. square, rhombus, rectangular) cross-sectional shape which is complementary to the outer cross-sectional shape of the key 122. The elongate track 120 therefore has radial engagement structures in the form of a plurality (e.g. four) inner corners that are configured to align with and engage against the radial engagement structures provided by the four outer corners of the key 122. The engagement of these corners prevents radial slipping of the key 122 within the track passage 130.

The elongate track 120 is formed of a first track portion 132 and a second track portion 134 which are configured to mate to form the track passage. At its distal and proximal ends, the elongate track 120 terminates in a distal narrowed section 136a and a proximal narrowed section 136b sized to retain the key 122 within the track passage 130. During manufacture, the key 122 is therefore inserted within the first or second track portion 132, 134 before the first and section track portions 132, 134 are connected to retain the key 122 within the track passage 130.

In this embodiment, the first track portion 132 includes an enlarged section 138 for receiving the second track portion 134 therein. When connected, the second track portion 134 forms a close fit (e.g. interference fit) within the enlarged section 138, thereby forming the track passage 130 through both the first and second track portions 132, 134.

The key 122 and the elongate track 120 do not form a tight interference fit. Rather, these elements are sized and shaped to permit relative axial movement when the key 122 is within the track passage 130, to enable adjustment of the position of the torque transfer unit 116 on the flexible shaft. The elongate track 120 (and in particular its track passage 130) therefore has a length that is greater (e.g. at least three times greater) than a length of the key 122. The length of the track passage relative to the key 122 effectively defines the range of positions that the torque transfer unit 116 may be moved to.

The clamping element 124 is located at a proximal end of the interface joint 116 and is actuatable between a clamped position for clamping onto the flexible shaft to prevent axial movement of the elongate track 120 relative to the key 122 (which may be attached, in use, to the flexible shaft) and an unclamped position for unclamping the flexible shaft to thereby permit axial movement of the elongate track 120 relative to the key 122. The axial position of the torque transfer unit 116 may therefore be adjusted by unclamping the clamping element 124 and moving the elongate track to a different axial position relative to the key 122.

Figure 3A:
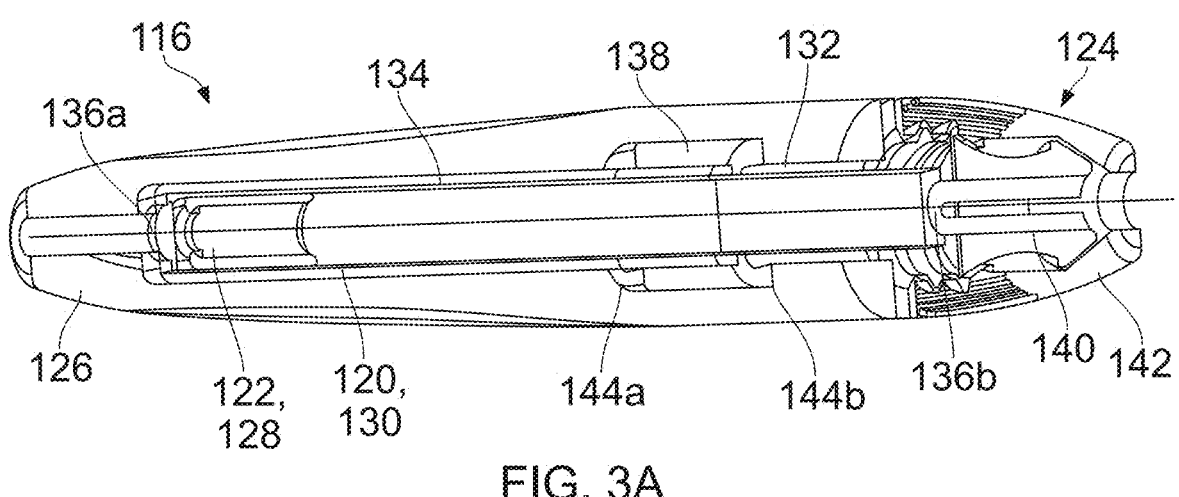
FIGS. 3A to 3C are side cutaway views of the torque transfer unit shown in FIG. 2, with the key shown at different locations within the elongate track.
Figure 3B:
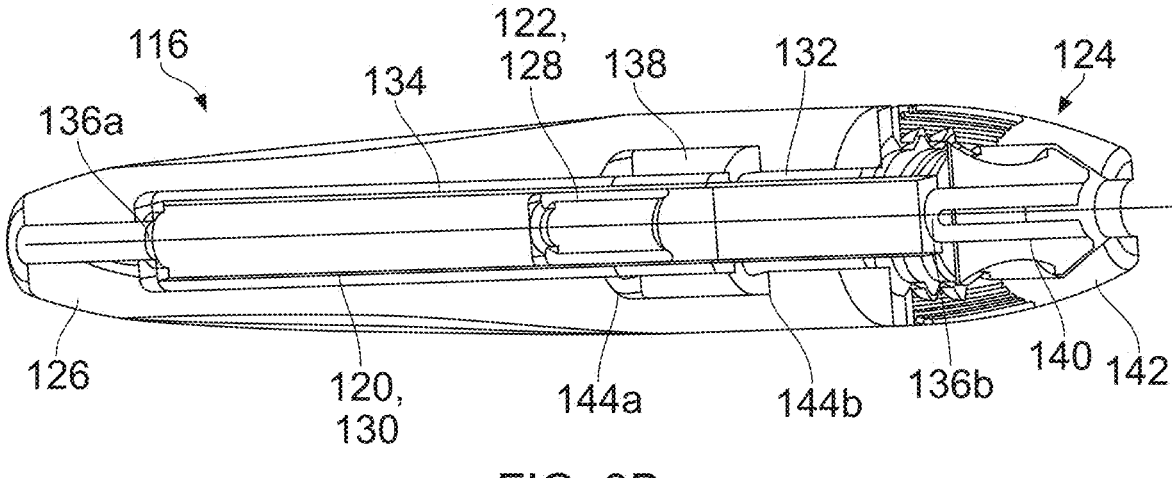
Figure 3C:
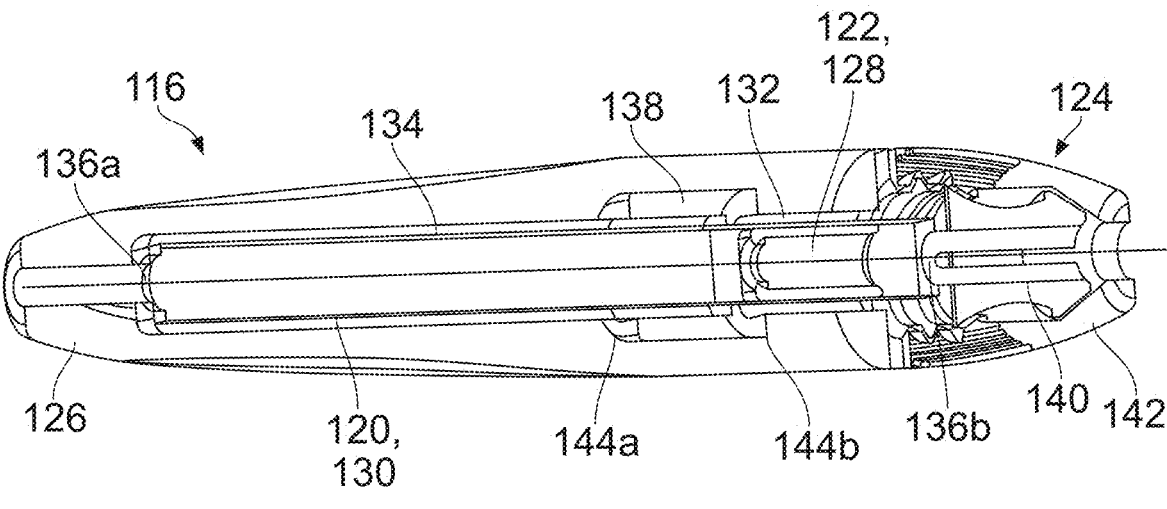

FIGS. 3A to 3C show example positions of the elongate track 120 relative to the key 122. In use, the key 122 may remain attached to the flexible shaft and therefore is not repositioned on the shaft during adjustment of the torque transfer unit 116. Rather, the key 122 may remain fixed while the rest of the torque transfer unit 116 is moved around it. Once the torque transfer unit 116 is in the desired location, the clamping element 124 may then be actuated to the clamped position to retain the torque transfer unit 116 in place.

In this embodiment, the clamping element 124 is rotatably actuatable. The clamping element 124 includes a collet 140 and an actuating element 142 (as best shown in FIG. 4). The clamping element 124 is attached to a proximal end of the elongate track 120. The collet 140 defines a clamping passage for the flexible shaft to extend through. The actuating element 142 is rotatably actuatable (e.g. by the thumb/finger of a user) between the clamped position and the unclamped position to selectively tighten the passage of the collet 140 onto the flexible shaft.

The cover 126 is arranged around the elongate track 120 for improved ergonomics and ease of use. The cover 126 may be formed of a deformable/flexible material (e.g. silicone). In this embodiment, the cover 126 includes a gripping surface in the form of a plurality of indentations/grooves sized and shaped to be held by a user's thumb/finger.

On its outer surface, the elongate track 120 has axial and radial engagement structures configured to engage against the cover 126 to prevent radial and/or axial slipping relative thereto. In this embodiment, the elongate track 120 has an outer surface having a polygonal (e.g. square, rhombus, rectangular) cross-sectional shape that provides radial engagement structure(s) (e.g. four corners) which are configured to engage against an inner surface of the cover 126 to prevent radial slipping. Additionally, the enlarged section 138 of the first track portion 132 forms axial engagement structures 144a-b in the form of a protrusion/ledge at each (distal and proximal) end of the enlarged portion 138. The inner surface of the cover 126 is configured to closely conform to the outer shape of the elongate track 120 and therefore resists relative motion across the radial and axial engagement structures, preventing radial and axial slipping of the cover 126 relative to the track 120.

FIG. 5 shows a torque transfer unit 116 positioned on a flexible shaft 112 outside of a surgical scoping device 114.

As shown by the arrow in FIG. 5, the clamping element 124 (and in particular the actuating element 142) is rotatable about the longitudinal axis to actuate from an unclamped to a clamped position. It may be advantageous to position the torque transfer unit 116 as close as possible to the scoping device 114, in order to provide optimal control over the instrument tip at the distal end of the scoping device. However, since the key 122 is preferably fixed to the flexible shaft 112, the positions over which the torque transfer unit 116 may be adjusted are constrained by the fixed position of the key 122 on the flexible shaft 112. Therefore, in order to enable use with a variety of surgical scoping devices 114 (which may each have different lengths), it may be desirable to provide a kit of parts having a plurality of flexible shafts 112, each flexible shaft 112 being connected to a respective key 122 for a torque transfer unit 116 at a different position along the flexible shaft 112. This may help to provide a kit that is optimal for use with a variety surgical scoping devices having different lengths, since a shaft may be selected that has a key attached to it at a position that closely corresponds to a length of the desired scoping device 114.

Figure 6:
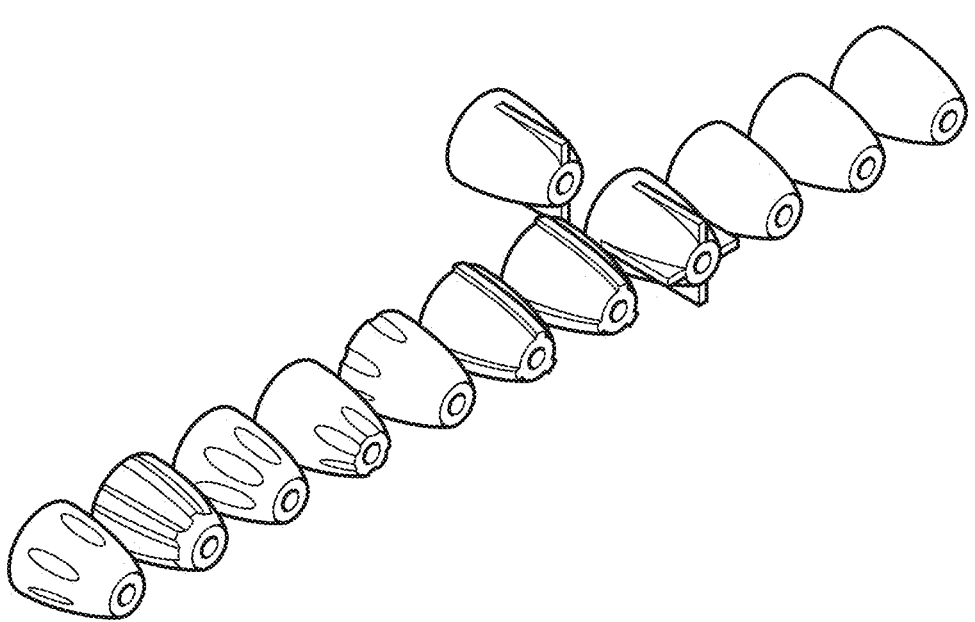
FIG. 6 is a perspective view of variant actuating elements suitable for use with the torque transfer unit shown in FIG. 2.

FIG. 6 shows a perspective view of a plurality of variant actuating elements suitable for use with the torque transfer unit 116 shown in FIGS. 1 to 5. The variant actuating elements are similar to the actuating element 142, but show a variety of different gripping surfaces, e.g. with each actuating element having a plurality of indentations, ribs, or wings radially distributed around and axially extending along the actuating element, or with similar actuating elements including no gripping surface at all.

Figures 7A, 7B:
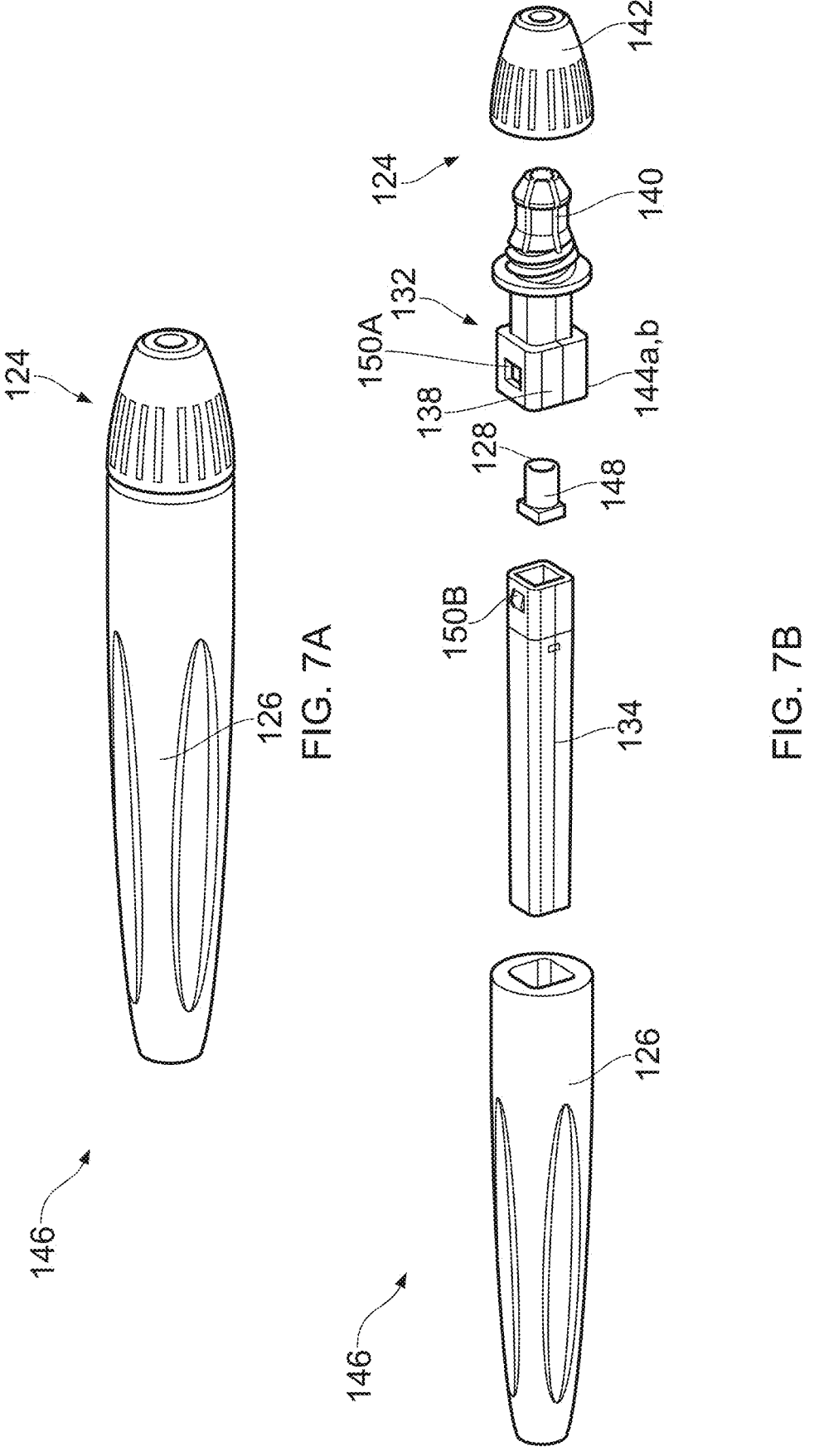
FIGS. 7A and 7B are side and exploded views, respectively, of an alternative torque transfer unit that it is an embodiment of the invention.

FIGS. 7A and 7B show side and exploded views, respectively, of an alternative torque transfer unit that is an embodiment of the invention. The torque transfer unit 146 is similar to the torque transfer unit 116 of FIGS. 2 to 5 and includes similar reference numerals to denote similar elements. However, the torque transfer unit 146 differs in the following respects.

The key 148 of the torque transfer unit 146 has a different shape than the key 122 of the torque transfer unit 116. In particular, whereas the key 122 had a rectangular (e.g. square) cross-sectional outer shape along its full axial length, the key 148 varies in cross-sectional shape along its axial length, varying from a rectangular (e.g. square) section to a circular section.

Further, the torque transfer unit 146 has a first snap-fit feature 150A on the first track portion 132 (in particular, the enlarged section 138 thereof), and a complementary second snap-fit feature 150B on the second track portion 134. The first and second snap-fit features 150A-B are configured to engage each other to facilitate interconnection of the first and second track portions 132, 134 in order to form the elongate track.

FIG. 8 shows a side view of a torque transfer unit 150 according to another embodiment of the invention. In contrast to the threaded clamping element shown in the previous embodiments, the torque transfer unit 150 has a clamping element that comprises a torsional spring 152. An example of a suitable torsional spring 152 is shown in FIG. 9. The torsional spring 152 comprises an annular portion defining a clamping passage 154 for the flexible shaft 112 to extend through. The torsional spring 152 further includes two radially protruding portions, each of which includes a handle or grip 156 and forms a terminal end of the spring. These portions can be squeezed together to increase the size of the clamping passage 154, and thereby selectively unclamp the flexible shaft 112.

FIGS. 10A and 10B show perspective and side views, respectively, of an alternative torque transfer unit 158 incorporating a torsional spring 152 similarly to that of FIGS. 8 to 9, but differing in that the torque transfer unit 158 replaces the pair of handles 156 with an actuating element in the form of a single lever 160. In use, the lever 160 can be actuated (rotated) by the thumb of a user, about the axis of the shaft, as illustrated by arrow A in FIG. 10A. This motion expands the spring 152, thereby opening the clamping passage 154 to release the flexible shaft 112 and permit axial adjustment of the torque transfer unit.

Figure 11:
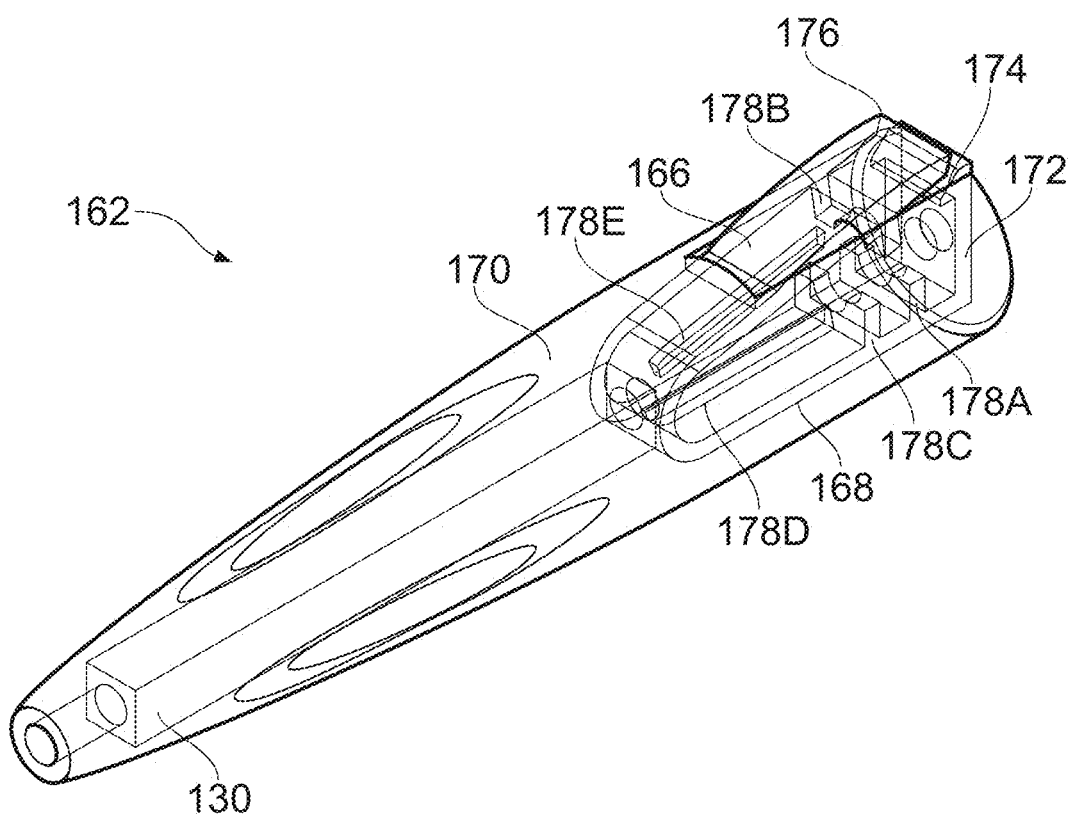
FIG. 11 is a perspective view of an embodiment torque transfer unit having a hinged clamping element.
Figure 12:
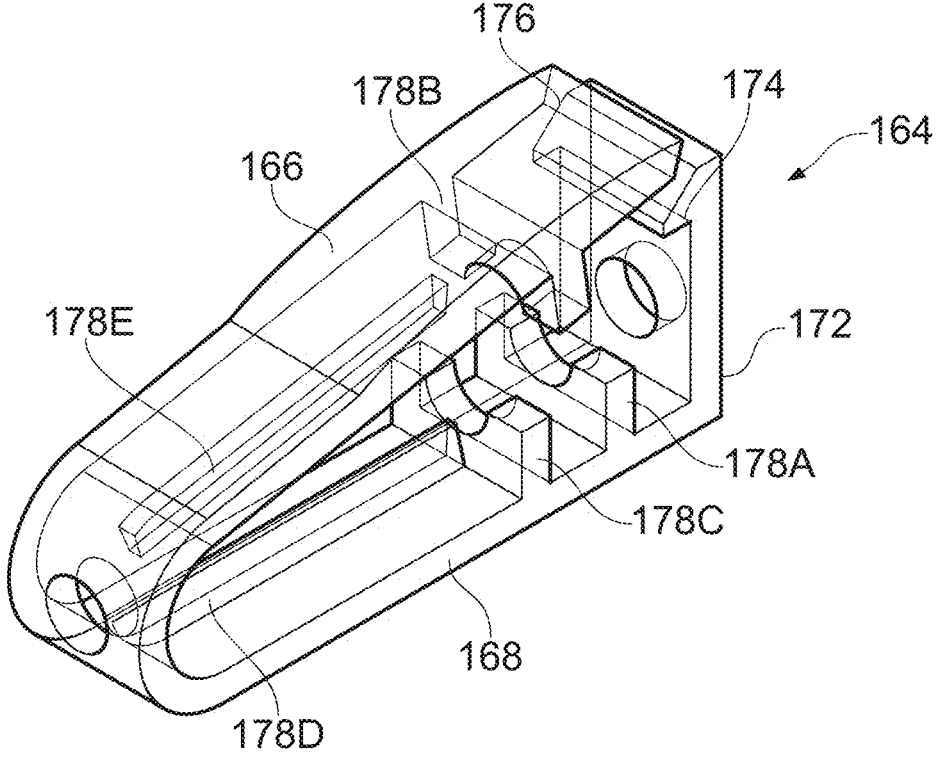
FIG. 12 is a perspective view of the hinged clamping element shown in FIG. 11.

FIG. 11 shows a perspective view of a torque transfer unit 162 according to another embodiment of the invention. The torque transfer unit 162 includes a hinged clamping element 164, which is shown in FIG. 12. The hinged clamping element 164 is a single unitary member (e.g. formed of plastic). The clamping element 164 comprises a first jaw 166 and a second jaw 168, which together form a unitary U-shaped structure. The first jaw 166 is configured to be pivoted towards or away from the second jaw 168, e.g. due to the first jaw 166 being relatively pliant (e.g. due to its material and/or shape). A junction between the first and second jaws 166 and 168 includes an aperture for conveying the flexible shaft therethrough.

The torque transfer unit includes a cover 170 which is similar to the cover 126 of the previous embodiments, but differs in that the cover 170 includes include a cut-out for accommodating the pivotal movement of the first jaw 166. The hinged clamping element 164 is retained within the cover 170, with the jaws 166, 168 opening towards a proximal end of the cover 170. In this embodiment, an inner surface of the cover 170 defines the track passage 130, i.e. the cover 170 is unitary with the elongate track. The torque transfer unit 162 further includes a key (not shown) that is axially movable within and rotatably fixed relative to the track passage 130, in a similar manner to the previous embodiments.

The clamping element 162 further includes a retaining member 172 which extends from a proximal end of the second jaw 168 towards a proximal end of the second jaw 166, across the open end of the U-shaped structure. The retaining member 172 includes an aperture for receiving the flexible shaft therethrough. The retaining member 172 is unitary with the first and second jaws 166 and 168. The retaining member 172 is pliant so that it may be actuated (pivoted) by a user bending the retaining member 172 (proximally) away from the jaws 166 and 168. Upon release by the user, the retaining member 172 is configured to resiliently snap-back to its original upright position (i.e. the position shown in FIGS. 11 and 12). A first end of the retaining member 172 (proximal to the first jaw 166) includes a hook 174 for engaging against a free (proximal) end 176 of the first jaw 166 when the first jaw 166 is pushed (pivoted) towards the second jaw 168.

In use, to actuate from an unclamped position (shown in FIGS. 11 and 12) to a clamped position (not shown), the user may bend the retaining member 172 proximally, so that it pivots relative to the second jaw 168. This movement is facilitated by the fact that the retaining member 172 is located at a proximal end of the torque transfer unit 162, thereby providing intuitive and simple adjustment. While the retaining member 172 is bend proximally, the user may push the first jaw 166 towards the second jaw 168, such that the free end 176 of the first jaw 166 slides past the hook 174. The user may then release the retaining member 172, allowing the retaining member to 'snap-back' and retain the first jaw 166 in place due to the engagement of the hook 174 against the free end 176.

In this embodiment, the first and second jaws 166 and 168 each include one or more protrusions (or teeth) 178A-C that are configured to bear against the flexible shaft when the clamping element 162 is in the clamped position. The second jaw 168 includes a proximal tooth 178A and a distal tooth 178C, and the first jaw 166 includes an intermediary tooth 178B located axially between the proximal and distal teeth 178A,C. Each tooth 178A-C has a curved inner profile shape to engage against the circumference of the flexible shaft. In the clamped position, the teeth 178A-C help to grip the flexible shaft between the jaws 166 and 168. Both jaws also include an elongate tooth or protrusion 178D,E extending along their distal ends, for facilitating grip of the flexible shaft.

Figure 13:
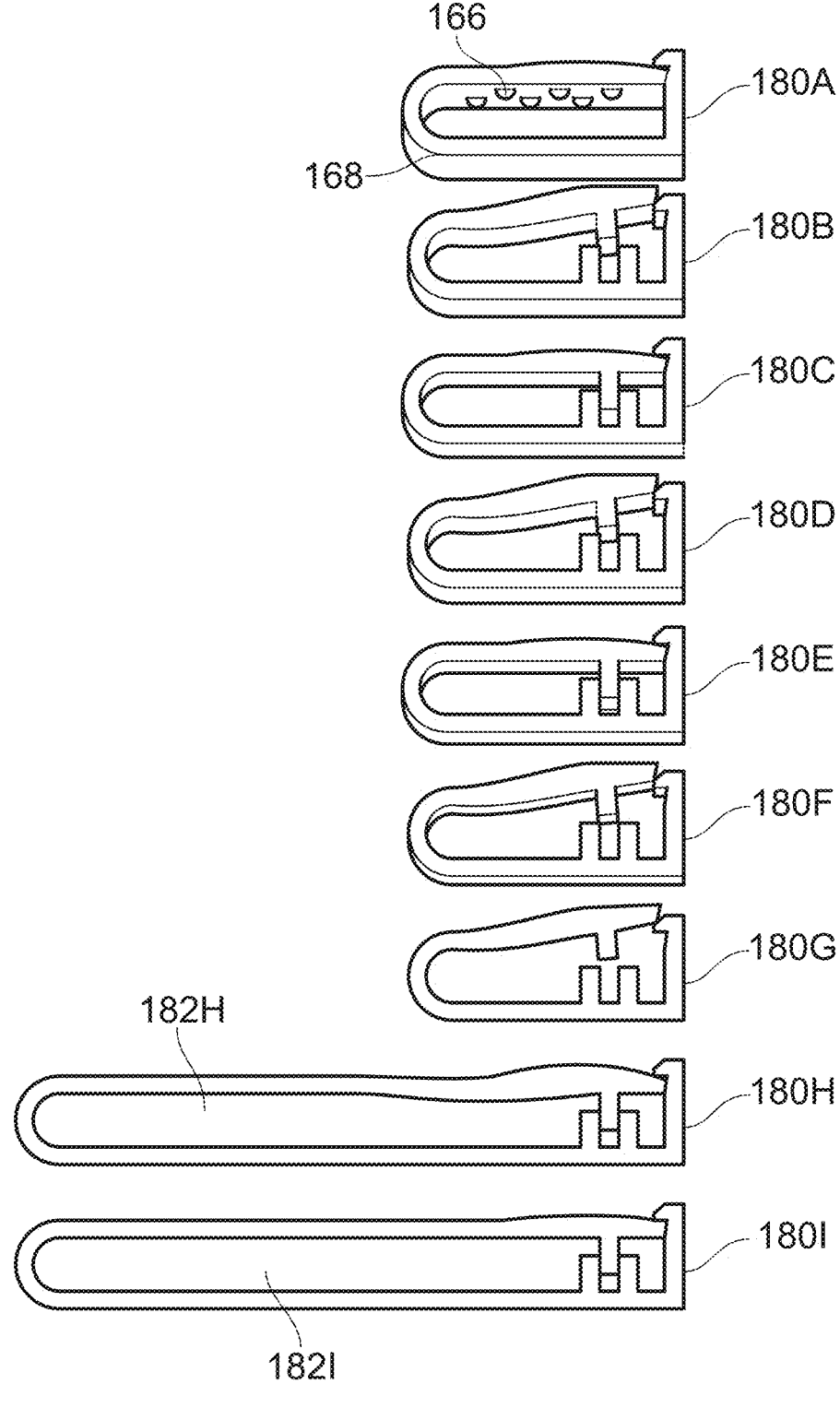
FIG. 13 is a side view showing variant hinged clamping elements.

FIG. 13 is a side view of a plurality of variant clamping elements 180A-G suitable for use with the torque transfer unit 162 of FIG. 11. The clamping element 180A differs from the remaining clamping elements primarily in the shape and configuration of the teeth. In particular, the clamping element 180A includes a plurality of teeth on the first jaw 166, and no teeth on the second jaw 168. The clamping elements 180B-G differ mainly in their shape and thickness, which can be modified to affect their pliancy.

FIG. 13 also shows two variant clamping elements 180H-I which are suitable with a modified torque transfer unit (not shown). These clamping elements 180H-I differ from the aforementioned clamping elements 180A-G in that the clamping elements 180H-I are unitary with an elongate track 182H-I defining a track passage for the key.

In FIG. 13, the clamping elements 180A, 180C, 180E, 180H, and 180I are shown in the clamped position, whereas the other elements are shown in an unclamped position.

Figure 14:
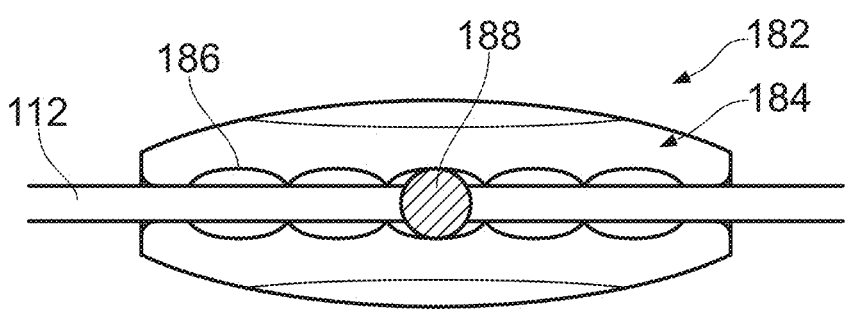
FIG. 14 is a side view of an embodiment torque transfer unit having a grippable member that is deformable to adjust a position of the torque transfer unit relative to the key.

FIG. 14 is a side view of torque transfer unit 182 according to another embodiment. The torque transfer unit 182 includes similar reference numerals to the previous torque transfer units to denote similar elements. However, the torque transfer unit 182 differs from those of the previous embodiments in that the torque transfer unit 182 does not include a distinct clamping unit. Rather, the torque transfer unit 182 comprises a grippable member 184 (similar to the cover 126 or 170) that also provides the function of the elongate track. The grippable member 184 is shaped on its inner surface to define a track passage 186, and is configured on its outer surface to provide a gripping surface.

Figure 15:
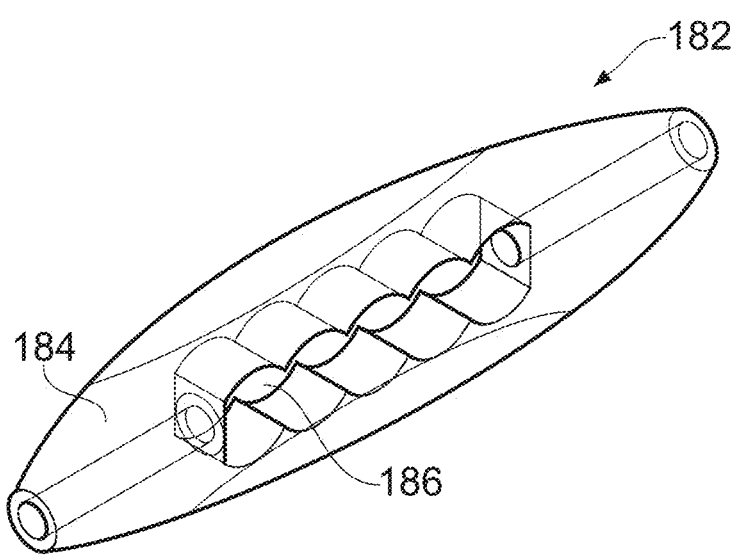
FIG. 15 is a perspective view of the torque transfer unit of FIG. 14, without showing the key or flexible shaft.

Similarly to the previous embodiments, the torque transfer unit includes a key 188 which is attachable to the flexible shaft 112 and moveable along the track passage 186. The key 188 and the elongate track (i.e. the grippable member 184) are configured to engage each other to inhibit relative rotation of the key and the track passage 186. This is best shown in FIG. 15, which illustrates that the track passage 186 has a square cross-sectional shape when viewed along the axis of the passage (i.e. from a proximal or distal end of the device). The key 188 likewise has a square cross-sectional shape when viewed from this direction, which is sized to inhibit (e.g. prevent) relative rotation with the track passage.

In contrast to the previous embodiments, the size of the track passage varies along its length. In particular, the track passage 186 has an undulating (scalloped) profile, providing a plurality of axial engagement structures (e.g. corners), which are configured to retain an axial position of the key, and which define a plurality of discrete positions in which the key 188 may be positioned. The key 188 has a complementary circular profile (when viewed from the side of the device), to facilitate axial positioning relative to the scalloped track.

In use, to adjust the axial position of the key relative to the track passage, the grippable member 184 can be pulled or pushed relative to the shaft 112. Since the grippable member 184 (and in particular the axial engagement structures) is deformable, under sufficient force by a user it can move past the key 188. The user may therefore actuate the torque transfer unit by exerting sufficient force on the grippable member 184 to deform and move it. Once in the desired position, the user can release the grippable member, which will retain the key in the desired axial position by virtue of the axial protrusions.

Figure 16:
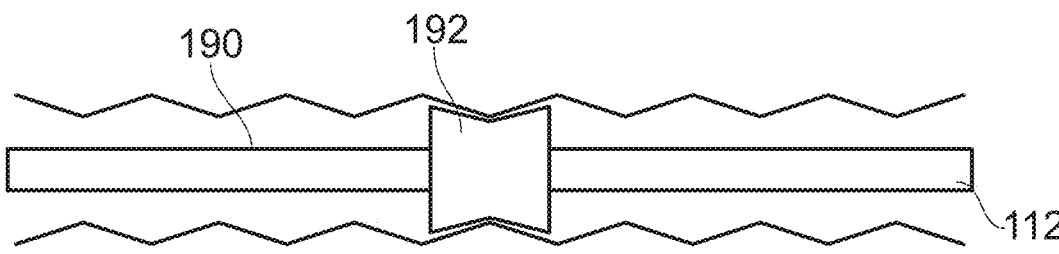
FIG. 16 is a side view of a variant track and key configuration suitable for the torque transfer unit of FIG. 14.

FIG. 16 is a side view of showing a variant track passage 190 and key 192, suitable for the torque transfer unit 184 of FIGS. 14 and 15. The track passage 190 differs from the track passage 186 in that the track passage 190 has a zig-zag profile rather than a scalloped profile (extending axially along the track passage). Correspondingly, the key 192 has an indented side profile configured to accommodate one of the protrusions of the zig-zag track passage. When viewed along the axial direction (i.e. from a proximal or distal end of the torque transfer unit), the key 192 and track passage 190 may have a square cross-sectional shape, similar to that of FIGS. 14-15, or may have any other shape configured to inhibit relative rotation (e.g. any non-circular shape).

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

REFERENCE NUMERALS

100 electrosurgery system
  102 generator
  104 interface cable
  106 interface joint
  108 fluid delivery apparatus
  electrosurgical instrument
    112 flexible shaft
    118 instrument tip
  107 fluid supply cable
  114 surgical scoping device
  116, 146, 150, 158, 162, 182 torque transfer unit
    120 elongate track
      130 track passage
        136*a-b* narrowed section
      132 first track portion
        138 enlarged section
        144*a-b* axial engagement structure(s)
      134 second track portion
  122, 148, 188, 192 key (e.g. collar)
    128 collar passage
  124 clamping element (collet)
    140 threaded collet
    142 actuating element
    152 torsional spring
      154 clamping passage
      156 handles
      160 lever
  164, 180A-I clamping element (hinged)
    166 first jaw
      176 free end
      178B intermediary tooth/protrusion
      178E elongate tooth/protrusion
    168 second jaw
      178A proximal tooth/protrusion
      178C distal tooth/protrusion
      178D elongate tooth/protrusion
    172 retaining member
      174 hook
  126, 170, 184 cover/grippable member
    186, 190 track passage

The invention claimed is:

1. A torque transfer unit for rotating a flexible shaft, the torque transfer unit comprising:
  an elongate track defining a track passage;
  a key attachable to the flexible shaft and movable along the track passage, the key and the elongate track being configured to engage each other to inhibit relative rotation of the key and the track passage; and
  a clamping element connectable to the elongate track and actuatable to selectively adjust an axial position of the key relative to the track passage, the clamping element being actuatable between:
    a clamped position for clamping onto the flexible shaft to thereby prevent axial movement of the elongate track relative to the key; and
    an unclamped position for unclamping the flexible shaft to thereby permit axial movement of the elongate track relative to the key.

2. The torque transfer unit according to claim 1, wherein the clamping element has a gripping surface to facilitate grip by a user.

3. The torque transfer unit according to claim 1, wherein the clamping element is rotatably actuatable between the clamped position and the unclamped position.

4. The torque transfer unit according to claim 1, wherein the clamping element comprises a resilient member that is resiliently biased towards the clamped position.

5. The torque transfer unit according to claim 1, wherein the key is a collar defining a collar passage for the flexible shaft to extend through.

6. The torque transfer unit according to claim 1, wherein an outer surface of the key has a rectangular cross-sectional shape, and an inner surface of the elongate track has a complementary rectangular cross-sectional shape for inhibiting relative rotation with the key.

7. The torque transfer unit according to claim 1, wherein the track passage terminates in a narrowed section for retaining the key along the track passage.

8. The torque transfer unit according to claim 1, wherein the elongate track has a length that is at least three times longer than a length of the key, more preferably at least four times longer than the length of the key, more preferably at least five times longer than the length of the key.

9. The torque transfer unit according to claim 1, wherein the clamping element defines a clamping passage for the flexible shaft to extend through, wherein the clamping element is actuatable to selectively tighten the clamping passage onto the flexible shaft.

10. The torque transfer unit according to claim 9, wherein the clamping element is a collet-type clamp.

11. The torque transfer unit according to claim 9, wherein the clamping element comprises:

a first jaw and a second jaw, the first jaw being movable relative to the second jaw to tighten the clamping passage onto the flexible shaft; and a retaining member that is actuatable to retain the first jaw in the clamped position or to release the first jaw from the clamped position.

12. The torque transfer unit according to claim 1, further comprising an outer cover around the elongate track, the cover including a gripping surface to facilitate grip by a user.

13. The torque transfer unit according to claim 12, wherein an outer surface of the elongate track and an inner surface of the cover are configured to engage each other to inhibit rotation or axial movement of the elongate track relative to the cover.

14. The torque transfer unit according to claim 1, wherein the elongate track comprises a first track portion and a second track portion, the first and second track portions being mutually connectable to form the elongate track.

15. The torque transfer unit according to claim 14, wherein the first track portion comprises an enlarged section for receiving and connecting with the second track portion.

16. A torque transfer unit for rotating a flexible shaft, the torque transfer unit comprising:

an elongate track defining a track passage;

a key attachable to the flexible shaft and movable along the track passage, the key and the elongate track being configured to engage each other to inhibit relative rotation of the key and the track passage; and an axial engagement structure along the track passage, the axial engagement structure being configured to engage against the key to inhibit relative axial movement of the key past the engagement structure;

wherein the torque transfer unit is actuatable to selectively adjust an axial position of the key relative to the track passage by sliding the elongate track relative to the key to overcome a resistive frictional force between the axial engagement structure and the key.

17. The torque transfer unit according to claim 16, wherein the elongate track is resiliently deformable between a non-deformed state in which the axial engagement structure inhibits relative movement of the elongate track past the key, and a deformed state in which the elongate track is slidable past the key.

* * * * *